US00PP08773P

United States Patent [19]

Fruehwirth

[11] Patent Number: Plant 8,773

[45] Date of Patent: Jun. 7, 1994

[54] POINSETTIA PLANT "559"

[75] Inventor: Franz Fruehwirth, Encinitas, Calif.

[73] Assignee: Paul Ecke Ranch, Inc., Encinitas, Calif.

[21] Appl. No.: 59,615

[22] Filed: May 7, 1993

[51] Int. Cl.[5] ..... A01H 5/00

[52] U.S. Cl. ..... Plt./86.4

[58] Field of Search ..... Plt. 86.4

[56] References Cited

U.S. PATENT DOCUMENTS 4,724,276 2/1988 Ecke, Jr. ..... 47/58

*Primary Examiner*—James R. Feyrer

*Attorney, Agent, or Firm*—Arnold, White & Durkee

[57] ABSTRACT

Poinsettia "559" is a new cultivar, distinguished by unusually smooth, rich red flower bracts, dark green foliage and self-branching characteristics. The new plant produces a very desirable branched flowering pot plant. Poinsettia "559" is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar, "559", originated as an induced self-branching sport of a seedling known as "H-18" (not patented) in my greenhouse in Encinitas, Calif. 'H-18' is a proprietary plant and there are no specimens in the public domain. It was selected because of its unusually smooth, large, bright, rich red flower bracts, and dark green foliage and self-branching characteristics; traits which distinguish it from other poinsettia cultivars, and seem to make it a desirable plant for commercial greenhouse production. After selection, "559" was vegetatively reproduced from stem cuttings for test purposes in Encinitas, Calif. By subjecting clones of this plant to successive generations of vegetative propagation, it was demonstrated that the distinctive characteristics of "559" held true from generation to generation.

DESCRIPTION OF THE PHOTOGRAPHS

Poinsettia "559" is illustrated in the accompanying color photographs. The upper photo is a side view of 3 single stem plants per pot in full flower. Evidence of self-branching can be seen in the flowering axillary branches beneath the upper canopy of bracts. The lower photo is a top view of the same plants showing flower and bract formation.

DESCRIPTION OF THE PLANT

The following is a detailed description of this new poinsettia as observed in Encinitas, Calif., U.S.A. during Dec. 1992. Observations were recorded from flowering plants, grown as 3 single stem plants per pot. The pot was 14 cm in diameter and 11 cm in height. Color designations are compared to the 1986 edition of R.H.S. Colour Chart, first published in 1966 by The Royal Horticultural Society, London, England.

THE PLANT

Origin: Sport of a seedling. The sport was induced by application of the procedures set forth in U.S. Pat. No. 4,724,276 (incorporated by reference) to the seedling plant. Root stock used was Angelika (U.S. Plant. Pat. No. 5,492).

Classification:

*Botanic.*—*Euphorbia pulcherrima* Willd.

*Common name.*—Poinsettia.

*Cultivar name.*—"559".

Form: Shrub.

Height: Medium.

Growth habit: As a single stemmed plant, upright and vigorous with self-branching side shoots. The application of a chemical growth retardant may be needed to restrict height for commercial pot plant production. I observed 3 unpinched plants in a pot with an overall height of 48 cm and an overall width of 48 cm. The bract diameter of individual flowers was 34 cm.

Branching: Axillary branches will develop and terminate in a flower without pinching. However, it is usually desirable to pinch "559" before flower induction and remove all terminal dominance. Then, all axillary branches will develop uniformly and at a faster rate.

Growth rate: Rooting of stem cutting occurs in 12–18 days under intermittent mist. The plant will flower in about nine weeks under continuous long night conditions and night temperatures of about 16–18 degrees C.

Foliage: The foliage is clean and uniformly dark green from bottom to top of the plant. The leaves are of medium size, leaf blades typically being 13–15 cm long and about 11–12 cm wide with leaf petioles 4–6 cm long.

*Leaf shape.*—Typical leaves are generally ovate with obtuse bases and acuminate tips. Leaf margins are lobed with 1 or 2 indentations on each side of the leaf blade.

*Color.*—Upper side — Dark green, darker than RHS 147A. Under side — Green, near RHS 147B.

*Retention.*—The foliage lasts extremely well even under low light intensities in the consumer's home.

Bracts: Generally there were 18–21 very smooth, rich red bracts of various sizes subtending the cyathia. The primary bracts have blades typically 18 cm long and 12 cm wide with petioles about 3 cm long.

*Shape.*—Primary bracts are ovate with acute bases and acuminate tips. Primary bract margins are lobed with 1 or 2 indentations on either side of the bract. Secondary bracts are elliptic, of various size and have entire margins.

*Color.*—Upper side — Rich, bright red, between RHS 45A-B. Under side — Light red, near RHS 45D.

Flowers: Generally, 15–18 cyathia (flowers) are present when the plant is in full bloom. Each cyathium is about 7 mm long and 6 cyathium mm wide, green in color, and fringed with red at the distal end. A yellow nectar cup with reddish lips protrudes from the side of each cyathium. The flower pedicel is also green and about 6 mm in length. The stamens protruding from the cyathia are dark red. The anthers are bifurcate; the pollen is yellow and copious. The stigmas are dark red and trifurcate. Cyathium retention is better than average, lasting three weeks beyond fully mature flowers.

*Nectar exudate.*—Abundant.

*Seeds.*—Self-incompatible.

*Fertility.*—Not observed.

Post production: Poinsettia "559" is resistant to epinasty after being confined to shipping containers and recovers rapidly if the plant does become epinastic.

What is claimed is:

1. A new and distinct Poinsettia cultivar, substantially as herein shown and described, distinguished by its unusually smooth, large rich red flower bracts, dark green foliage, and self-branching characteristics.

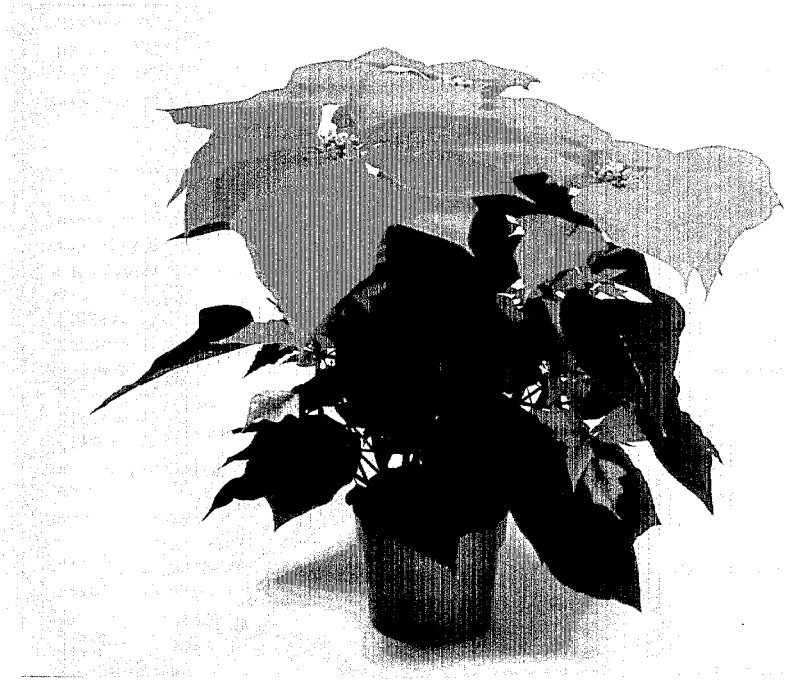
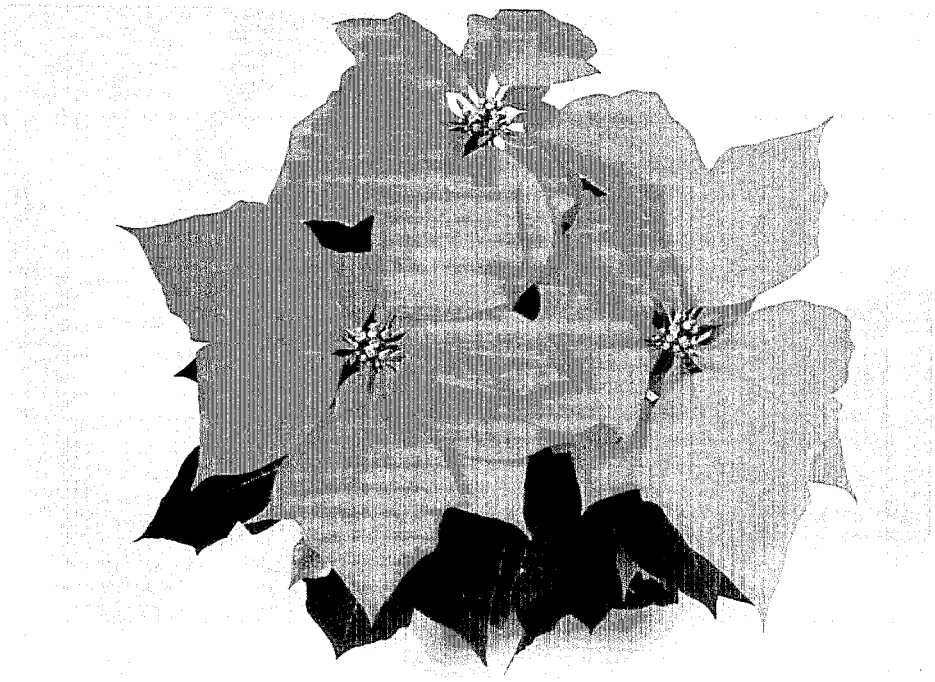

* * * * *